United States Patent [19]

Rautenbach

[11] 4,139,777
[45] Feb. 13, 1979

[54] CYCLOTRON AND NEUTRON THERAPY INSTALLATION INCORPORATING SUCH A CYCLOTRON

[76] Inventor: Willem L. Rautenbach, 18 Unie Ave., Stellenbosch, Cape Province, South Africa

[21] Appl. No.: 738,483

[22] Filed: Nov. 3, 1976

[30] Foreign Application Priority Data

Nov. 19, 1975 [ZA] South Africa .................. 75/7266

[51] Int. Cl.$^2$ .............................................. G21G 4/02
[52] U.S. Cl. ..................................... 250/499; 313/615
[58] Field of Search .................... 250/499, 501, 502; 313/61 R, 61 S

[56] References Cited

U.S. PATENT DOCUMENTS

| 3,609,369 | 9/1971 | Croitora | 250/501 |
| 3,786,258 | 1/1974 | Schmidt | 250/501 |
| 3,925,676 | 12/1975 | Bigham et al. | 250/499 |

Primary Examiner—Alfred E. Smith
Assistant Examiner—B. C. Anderson

[57] ABSTRACT

A cyclotron suitable for use in neutron therapy, and comprising a pair of opposed, spaced pole shoes having their adjacent inner surfaces defining an accelerator zone, an electromagnetic coil system, at least one hollow accelerating dee electrode positioned in the accelerator zone, and having a radio-frequency resonator associated therewith, a magnet yoke shaped to substantially enclose the accelerator zone and constitute a neutron attenuation shield for neutrons produced in the cyclotron, a vacuum chamber enclosing the accelerator zone and each dee electrode, means for providing charged particles for acceleration within the accelerator zone, a target zone for a target device, and a neutron beam outlet in the magnet yoke for emission of a neutron beam produced in the cyclotron. The cyclotron includes auxiliary neutron shield means in the forward peak zone of a neutron beam produced in the cyclotron to attenuate neutron and gamma radiation in the forward peak zone to a patient tolerable level. Each radio-frequency resonator is enclosed within the magnet yoke. The cyclotron may have pivot means for pivotally mounting the cyclotron to allow variation of the direction of a neutron beam during use. The disclosure further relates to a neutron therapy installation incorporating such a cyclotron.

28 Claims, 12 Drawing Figures

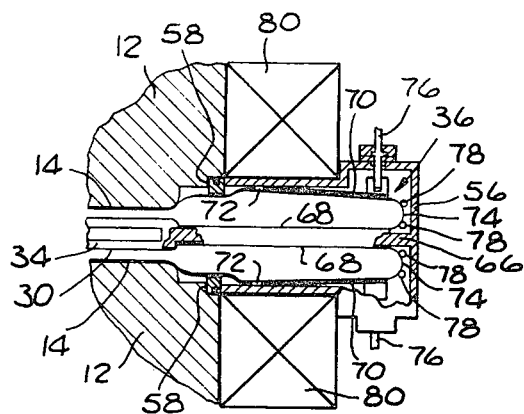
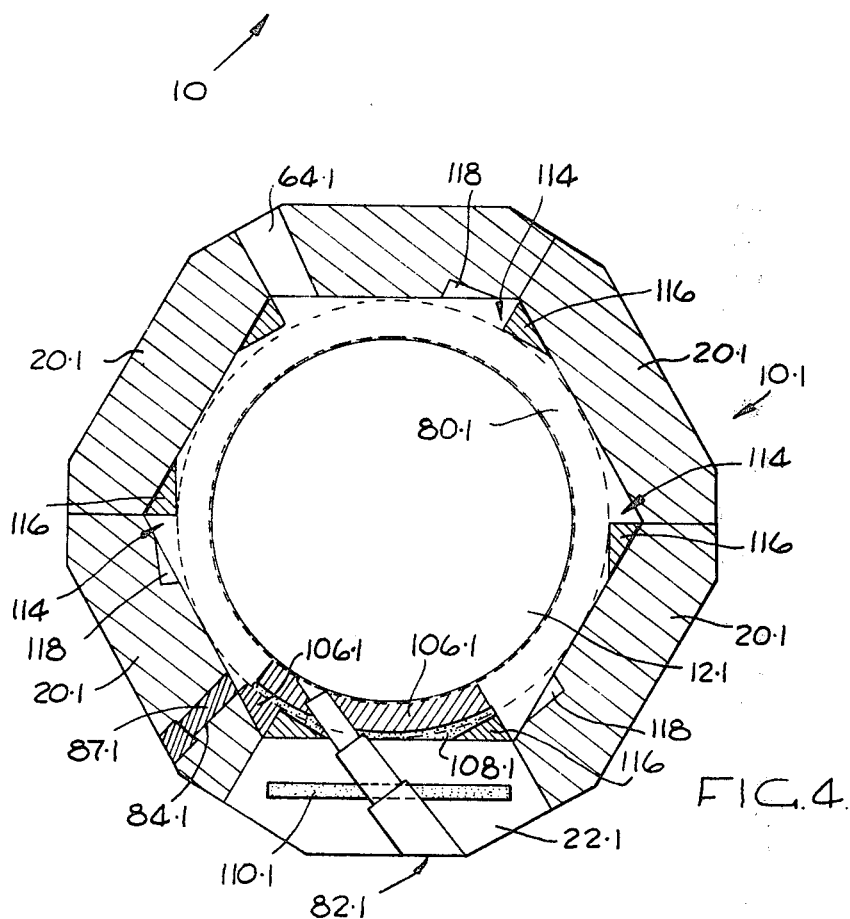

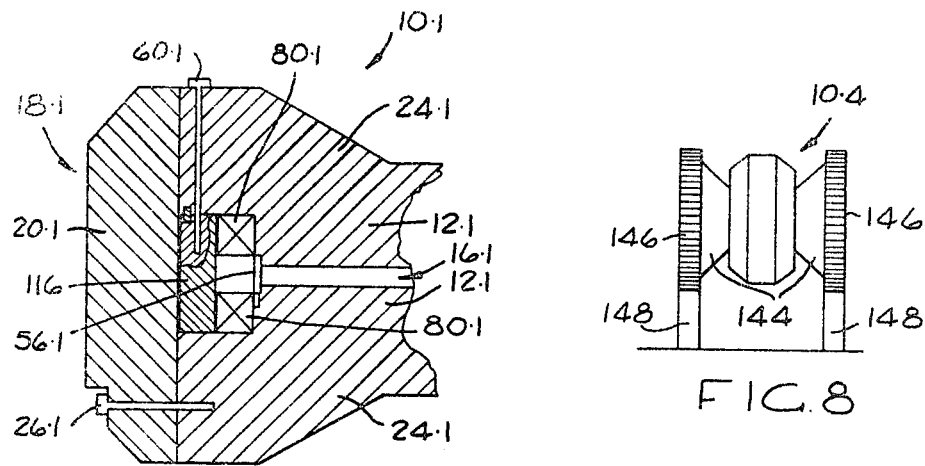
FIG.5.
FIG.8
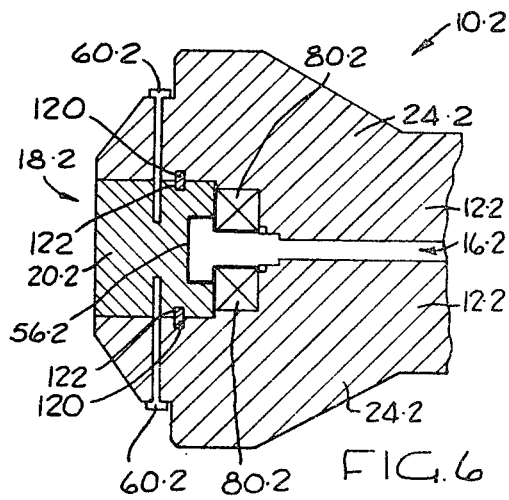
FIG.6
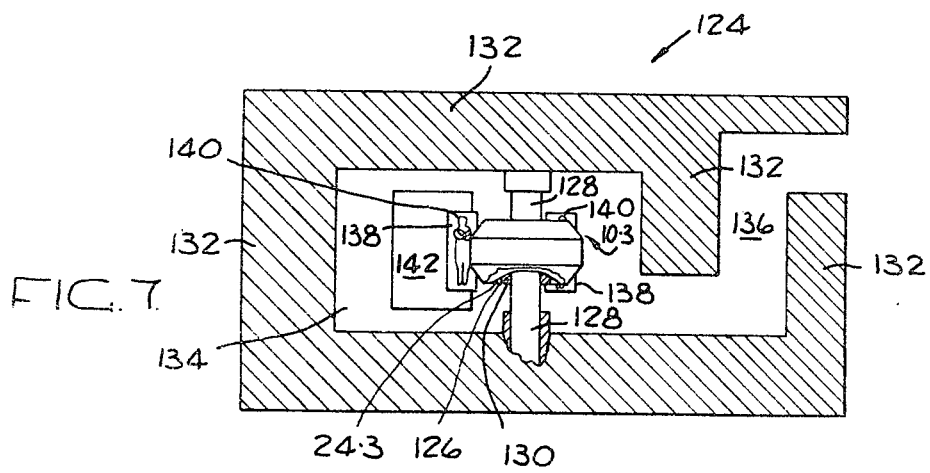
FIG.7

CYCLOTRON AND NEUTRON THERAPY INSTALLATION INCORPORATING SUCH A CYCLOTRON

This invention relates to a cyclotron and to a therapy installation. More particularly, this invention relates to a cyclotron suitable for use in neutron therapy, and to a neutron therapy installation including such a cyclotron.

According to the invention there is provided a cyclotron suitable for use in neutron therapy, and comprising:
(a) a pair of opposed, spaced pole shoes having their adjacent inner surfaces defining an accelerator zone,
(b) an electromagnetic coil system,
(c) at least one hollow accelerating dee electrode positioned in the accelerator zone, and having a radio frequency resonator associated therewith,
(d) a magnet yoke shaped to substantially enclose the accelerator zone and constitute a neutron attenuation shield for neutrons produced in the cyclotron,
(e) a vacuum chamber enclosing the accelerator zone and each dee electrode,
(f) means for providing charged particles for acceleration within the accelerator zone,
(g) a target zone for a target device, and
(h) a neutron beam outlet in the magnet yoke for emission of a neutron beam produced in the cyclotron.

In an embodiment of the invention, the cyclotron may be in the form of an isochronous cyclotron having an isochronous magnetic field with at least three hills and valleys defined by the adjacent inner surfaces of the pole shoes.

In this embodiment of the invention, the hills and valleys may conveniently be radial hills and valleys.

Further, in this embodiment of the invention, the cyclotron may conveniently have a dee electrode positioned in each valley, with each dee electrode having a radiofrequency resonator associated therewith.

By having the dee electrodes positioned in the valleys, the width of the pole gap can be decreased and compactness of the cyclotron can thus be improved.

In this specification, by a "hollow accelerating dee electrode" is meant a hollow accelerating electrode of conventional type, having an appropriate configuration for the number and positioning of the electrodes in a particular cyclotron application.

Where a plurality of dee electrodes are employed, the dee electrodes may be adapted to be operated in phase or out of phase with each other.

Where the dee electrodes are to be operated in phase with each other, they may conveniently be connected to each other at the centre of the accelerator zone.

The cyclotron may have a suitably positioned transmission bore for a radio-frequency energy transmission line, for each dee electrode.

In an embodiment of the invention, the cyclotron may have a transmission bore extending along the polar axis of one of the pole shoes, with the transmission bore having a radio-frequency transmission line located in the transmission bore and connected to the dee electrodes at the centre of the accelerator zone, and with the transmission line having coupling means for coupling the transmission line to a radio-frequency power source.

The coupling means may be of any suitable type. Thus, for example, the coupling means may be in the form of capacitor or inductive coupling means, a swivel coupling connection, or the like.

Connection of the dee electrodes to the transmission line at the centre of the accelerator zone, can assist in axially stabilising the dee electrodes to combat frequency variations under pulsed dee voltages during use.

The means for providing charged particles for acceleration within the accelerator zone, may be any suitable conventional means.

Thus, for example, the means may comprise injection means for the injection of charged particles into the accelerator zone or a loading passage for loading the cyclotron with a suitable ion source.

By having the magnet yoke shaped to substantially enclose the accelerator zone, the distribution of the magnet steel is such as to facilitate the construction of a compact cyclotron in accordance with this invention. In addition, the magnet yoke will thus constitute a neutron attenuation shield for neutrons produced in the cyclotron.

In general, for a cyclotron in accordance with this invention, having a sufficient energy to provide a fast neutron beam suitable for use in neutron therapy, once the magnet yoke has a sufficient wall thickness for the magnetic flux requirements, the wall thickness will be sufficient to attenuate neutron fluxes of low intensity coming off at wide angles to the forward neutron peak zone of a neutron beam produced in the cyclotron as well as stray neutrons arising in the cyclotron, to a patient tolerable level in a neutron therapy installation incorporating such a cyclotron.

Where deuterons are to be accelerated with the cyclotron of this invention, applicant believes that the minimum size of the cyclotron which will be required to produce a neutron beam suitable for neutron therapy, would correspond to a deuteron energy of about 20 to 30 MeV, and conveniently, about 35 MeV.

For a deuteron energy of this order, when the magnet yoke is sufficient for the magnetic flux requirements, the wall thickness should be sufficient for neutron attenuation other than in the forward peak zone, to a patient tolerable level in a neutron therapy installation.

For higher deuteron energies, the magnetic flux requirements will increase correspondingly, so that the wall thickness of the magnet yoke should again be sufficient for the above purpose.

However, for the acceleration of protons, applicant believes that the minimum size of the cyclotron which will be required to produce a neutron beam suitable for neutron therapy, would correspond to a proton energy of about 20 to 30 MeV, and conveniently about 35 MeV.

For a proton energy of a particular value, the radius of the outer orbit would be reduced by about 40% in relation to a deuteron energy of the same value, leading to an approximately 40% reduction in size of the cyclotron.

Thus, for the acceleration of protons, it will usually be necessary to increase the thickness of the magnet yoke over and above that dictated by the magnetic flux requirements to provide sufficient attenuation for the purpose specified above.

For the acceleration of Helium-3, the cyclotron would tend to have a size intermediate that of the corresponding proton and deuteron accelerating cyclotrons, and thus increased thickness of the magnet yoke over and above that dictated by the magnetic flux requirements, would usually be necessary.

For use in neutron therapy, auxiliary neutron shield means will be required in the forward peak zone of a neutron beam produced in the cyclotron, to shield the body of a patient being treated, against the intense flux of high energy neutrons in the forward peak zone of the neutron beam.

In one embodiment of the invention, the cyclotron of this invention may therefore be used for neutron therapy with an external auxiliary neutron shield provided in the forward peak zone of a neutron beam produced in the cyclotron, between the cyclotron and a patient to be treated.

In this embodiment, the external auxiliary neutron shield may be separate from the cyclotron, or may be mounted on the exterior of the cyclotron about the neutron beam outlet.

However, by using an external auxiliary neutron shield, the distance between an affected area of a patient to be treated, and the neutron beam generation zone within the cyclotron, is increased so that higher neutron production rates will be required for effective treatment.

In an alternative embodiment of the invention, the cyclotron may include auxiliary neutron shield means in the forward neutron peak zone of a neutron beam produced in the cyclotron.

The auxiliary neutron shield means may, for example, be sufficient to attenuate neutron and gamma radiation in the forward peak zone to provide a combined neutron and gamma radiation dose rate of less than about 3% of that in a neutron beam emitted from the neutron beam outlet during use.

In a specific example of the invention, the auxiliary neutron shield means may be sufficient to attenuate neutron and gamma radiation in the forward peak zone to provide a combined neutron and gamma radiation dose rate of less than about 2%, and conveniently less than about 1%, of that in a neutron beam emitted from the neutron beam outlet during use.

Gamma rays arise on a target during neutron beam production on the target, and also result from neutron attenuation in the magnet yoke.

In an example of the invention, the auxiliary neutron shield means may comprise a neutron attenuation shield and a neutron moderating shield.

The neutron attenuation shield may be of any conventional non-magnetic material such as, for example, copper, and may be mounted on the outer periphery of the magnet yoke and/or within the inner periphery of the magnet yoke in the forward peak zone.

The neutron moderating shield may be of any conventional type. It may thus, for example, comprise any suitable hydrogen containing moderating material, which may contain suitable known elements such as boron, cadmium, or the like, to capture thermal neutrons.

The neutron moderating shield may be provided on the outer and/or inner periphery of the magnet yoke and/or in a cavity within the magnet yoke, in the forward peak zone.

The auxiliary neutron shield means may further be provided by the magnet yoke having an increased thickness in the forward peak zone.

Where the auxiliary neutron shield means comprises part of the cyclotron, this provides the advantage that shorter distances can be employed between the neutron beam source within the cyclotron, and an affected area of a patient to be treated thereby allowing for lower neutron production rates. It is a further advantage that by having the auxiliary neutron shield means in close proximity to the neutron beam source, the mass of shielding required can be reduced, thereby allowing for a reduction of the mass of the cyclotron and for improvement of the compactness thereof. It is a further advantage that the auxiliary neutron shield means would tend to be the most radioactive part of the cyclotron and can therefore be replaced when necessary or can be removed to facilitate servicing.

The neutron beam outlet may conveniently be shaped to removably receive different size collimators to control the radiation field size of a neutron beam emitted from the neutron beam outlet.

The collimators may be made of any conventional material. Thus, for example, the collimators may be made of water extended polyester with our without metal loading, borated teak, or borated pressed wood.

In an embodiment of the invention, the vacuum chamber may conveniently be defined by the adjacent inner surfaces of the pole shoes and by an annular generally channel-shape member surrounding the accelerator zone and having its free edges sealingly secured to the opposed pole shoes.

The cyclotron may include internal vacuum pump means and/or may be adapted to be connected to external vacuum pump means, to maintain the required vacuum within the vacuum chamber.

Where the cyclotron includes internal vacuum pump means, the internal vacuum pump means may be provided at suitable intervals along the inner periphery of the magnet yoke, and may be of any suitable conventional type. Thus, for example, the internal vacuum pump means may comprise one or more cryogenic pumps or a combination of titanium sublimation and ion pumps.

Where the cyclotron is adapted for use with external vacuum pump means, the cyclotron may have a radial vacuum conduit extending radially through the magnet yoke and/or may have an axial vacuum conduit extending along the polar axis of one of the pole pieces, for connection to an external vacuum pump means.

Where the cyclotron includes a radial vacuum conduit, the conduit may conveniently be provided on the opposed side of the cyclotron to the neutron beam outlet and the vacuum conduit may be in the form of a maze to afford protection for a patient against stray neutrons escaping from the vacuum conduit.

The magnet yoke may conveniently comprise a plurality of separate yoke sections which together constitute the magnet yoke. Thus the yoke sections can be separately removed for replacement or to allow access to the interior of the cyclotron for maintenance purposes.

Each radio-frequency resonator may be of any suitable construction, and may be positioned to extend radially or circumferentially of the polar axis of the accelerator zone.

In an embodiment of the invention, each radio-frequency resonator may extend radially and may be enclosed within the magnet yoke. In this embodiment, each radio-frequency resonator may conveniently be enclosed within the vacuum chamber.

In this embodiment of the invention, each radio-frequency resonator may comprise a flat, narrow inner conductor plate mounted on the dee, and two flat, wider outer conductor plates on opposed sides of and laterally spaced from the inner conductor plate, with the outer conductor plates connected to the inner conductor plate by means of short circuit plates.

In this embodiment, each outer conductor plate may include a flexible hinge, each short circuit plate may be flexible, and frequency adjustment means may extend from each outer conductor plate sealingly through the walls defining the vacuum chamber, to allow for adjustment of the characteristic impedance of each radio-frequency resonator.

The electro-magnetic coil system may be of any conventional type and should include cooling means of any conventional type.

In an embodiment of the invention, the coil system may comprise two annular coils surrounding the pole shoes, with the coils located outside the vacuum chamber to permit the use of radiation resistant insulation material which is not necessarily vacuum compatible.

The cyclotron may, if necessary, include cooling zones associated with the pole shoes.

In an embodiment of the invention, each cooling zone may comprise walls arranged in a spiral to ensure a substantially even distribution of a cooling medium over the pole shoes irrespective of the inclination of the accelerator zone.

The adjacent inner surfaces of the pole shoes which define the accelerator zone and which are exposed to the dee electrode or electrodes, may be lined or coated with any conventional vacuum compatible corrosion-resistant non-magnetic layer. Thus, for example, the layer may comprise thin water cooled copper plates or copper electrolytically deposited on the adjacent inner surfaces of the pole shoes.

The target zone may comprise or include a target admission zone to allow admission of a suitable target device into the accelerator zone, and may include automatic sealing means of any conventional type. The target admission zone may conveniently extend radially through the magnet yoke.

The dee electrodes of the cyclotron may be arranged in relation to the neutron beam outlet and the target zone, so that a neutron beam produced in the cyclotron can be emitted from the neutron beam outlet without interfering unduly with the dee electrode or electrodes and particularly, so that the dee electrode or electrodes will not be directly in the forward peak zone of the neutron beam.

The cyclotron may have a target device positioned in the target zone. Alternatively the cyclotron may include a target device for admission through the target admission zone, and a removable shielding plug for shielding the admission zone.

The target device may comprise a target stem with a suitable target provided thereon.

The shielding plug may be of a suitable neutron shielding material, and may have one or more enlarged step formations towards its trailing end for shielding location in a target admission zone of a complementary configuration.

Each target device may have adjustment means to permit limited adjustment of the circumferential position of the target and of the extent to which a target projects into the accelerator zone of the cyclotron, thereby allowing for interception of an orbiting beam at differing circumferential positions and radial distances from its starting zone. Thus by appropriate adjustment, the peak of the neutron flux beam produced can be made to coincide with the axis of the neutron beam outlet.

The target device may be in the form of a stationary target device having conventional liquid cooling tubes leading through the target stem to the target. Alternatively, the target device may be in the form of a rotatable target device which can be liquid cooled by conventional means or, if the speed of proposed rotation is sufficiently high, may be radiation cooled.

The target of the target device may be of any suitable material. Thus, for example, it may be a beryllium target.

The cyclotron of this invention may, if desired, be provided with an outer neutron moderating layer of any suitable type, to moderate slow neutrons escaping from the magnet yoke.

In an embodiment of the invention, the outer neutron moderating layer may be provided by borated wood secured to the outer periphery of the cyclotron. In an alternative embodiment, the neutron moderating layer may comprise boron containing paraffin wax located within an outer shell about the cyclotron.

The cyclotron of this invention may be provided with a plurality of neutron beam outlets, and a target zone operatively positioned relatively to each neutron beam outlet.

Thus, for example, the cyclotron may be provided with two, three, or more neutron beam outlets and associated target zones.

Thus, during use, a neutron beam can be produced for emission out of any desired neutron beam outlet by appropriate movement of the target devices into or out of the accelerator zone within the cyclotron.

For each neutron beam outlet not in use at any time, a suitably shaped shielding member may be located therein, and a shielding plug may be located in its corresponding target admission zone.

While the cyclotron of this invention is particularly suitable for use in neutron therapy, it will be appreciated that when heated in a suitably biologically shielded chamber, the cyclotron can be used for isotope production.

The cyclotron of this invention may have pivot means for pivotally mounting the cyclotron to allow variation of the direction of a neutron beam emitted from the neutron beam outlet during use.

In one embodiment of the invention, the pivot means may comprise pivot bores in opposed sides of the cyclotron, for receiving pivot shafts to pivotally support the cyclotron.

In an alternative embodiment of the invention, the pivot means may comprise two pivot shafts extending outwardly from opposed sides of the cyclotron.

In this embodiment of the invention, each pivot shaft may have a support roller mounted thereon for pivotally supporting the cyclotron on suitable support rails.

Each support roller may conveniently be in the form of a gear wheel for supporting the cyclotron on suitable support rails in the form of linear gear rails having teeth to mesh with the gear wheel teeth.

In this embodiment of the invention, the linear gear rails may be horizontal or may be inclined to the horizontal.

The pivot means may conveniently have its polar axis extending normally to the plane of the accelerator zone along the polar axis of the cyclotron.

In a specific embodiment of the invention, the pivot means may comprise a pivot frame in which the cyclotron is mounted, the pivot frame having a pair of opposed supporting legs, with each supporting leg having a pivot bore for pivotally mounting the frame on a pair of support axles, and the pivot frame having a pivot beam mounted thereon, with the pivot beam having guide gear wheels mounted at its opposed ends to cooperate with a pair of curved, complementarily toothed guide rails positioned concentrically with the support axles to guide pivotal displacement of the cyclotron about the pivot bores.

The pivot bores may conveniently be positioned so that their axes will intersect the core of a neutron beam emitted from the neutron beam outlet during use, in the treatment zone of such a beam where the centre of an affected area of a patient to be treated, would be positioned during treatment. Thus, an isocentric therapy system would be provided.

In yet a further alternative embodiment of the invention, the pivot means may comprise a turntable to support the cyclotron on a surface for pivotal displacement about a vertical axis.

The invention further extends to a neutron therapy installation defined by biological shielding means, and having a cyclotron as described herein, mounted therein.

Where the cyclotron has pivot means, the installation may have complementary pivot support means for engaging with the pivot means.

Where the cyclotron has pivot means in the form of a turntable to support the cyclotron on the floor of a neutron therapy installation for pivotal displacement about a vertical axis, the installation may have a plurality of separate treatment rooms circumferentially spaced about the cyclotron, with each room having an access opening to register with the neutron beam outlet of the cyclotron.

The same arrangement may be provided for a neutron therapy installation for use with a cyclotron having a plurality of neutron beam outlets.

In this embodiment of the invention, the cyclotron may be mounted so that it is stationary, and has its polar axis extending vertically, and each separate treatment room may be in register with one of the neutron beam outlets.

With these arrangements, the rate of treatment can be increased since, while a patient is being treated in one of the separate treatment rooms, a patient can be set up for treatment in another of the treatment rooms.

The neutron therapy installation may include a separate servicing zone having collimator storage means for storing collimators when not in use.

The collimator storage means may conveniently include a rotatably mounted collimator holder for holding a plurality of collimators at circumferentially spaced intervals.

The holder may include transferring means for transferring collimators from and to the neutron beam outlet when such an outlet has been correctly positioned by pivotal displacement of the cyclotron.

Thus, when a particular collimator is to be replaced because it has become too radio-active, or because a differing size is required, this can be effected automatically by remote control in the servicing zone thereby reducing the risk of radiation contamination.

The therapy installation may include one or more plinths for supporting patients. The plinths may be of any conventional type, and may be vertically and/or laterally adjustable.

The cyclotron of this invention may be designed for the acceleration of charged particles in the form of deuterons, protons and helium-3.

Where the cyclotron of this invention is to be used in neutron therapy it may, for example, have a capacity to provide accelerated charged particles having an energy in the range of about 15 to 80 MeV deuterons, and conveniently at least about 35 MeV deuterons.

In the case of protons, the cyclotron may, for example, have a capacity to provide accelerated charged particles having an energy in the range of about 15 to 100 MeV protons, and conveniently at least about 35 MeV. In the case of helium-3, the cyclotron may, for example, have a capacity to provide accelerated particles having an energy in the range of about 20 to 100 MeV helium-3 particles.

Embodiments of the invention are now described by way of example with reference to the accompanying drawings. In the drawings:

FIG. 3 shows, to an enlarged scale, a fragmentary, partly sectional elevation through a plane normal to the plane of the accelerator zone, to illustrate details of the radio-frequency resonators of the cyclotron of FIGS. 1 and 2;

FIG. 4 shows a fragmentary, diagrammatic, sectional elevation through the plane of the accelerator zone of an alternative construction of an isochronous cyclotron in accordance with this invention;

FIG. 5 shows a fragmentary, diagrammatic, sectional elevation through a plane normal to the plane of the accelerator zone, of the cyclotron of FIG. 4;

FIG. 6 shows a fragmentary, diagrammatic, sectional elevation through a plane normal to the plane of the accelerator zone of yet a further alternative embodiment of an isochronous cyclotron in accordance with this invention;

FIG. 7 shows, to a reduced scale, a fragmentary, diagrammatic, partly sectional, plan view of a neutron therapy installation having a cyclotron in accordance with this invention, mounted therein;

FIG. 8 shows a diagrammatic, fragmentary, end elevation of a cyclotron in accordance with this invention, pivotally mounted in position;

Figure 1:
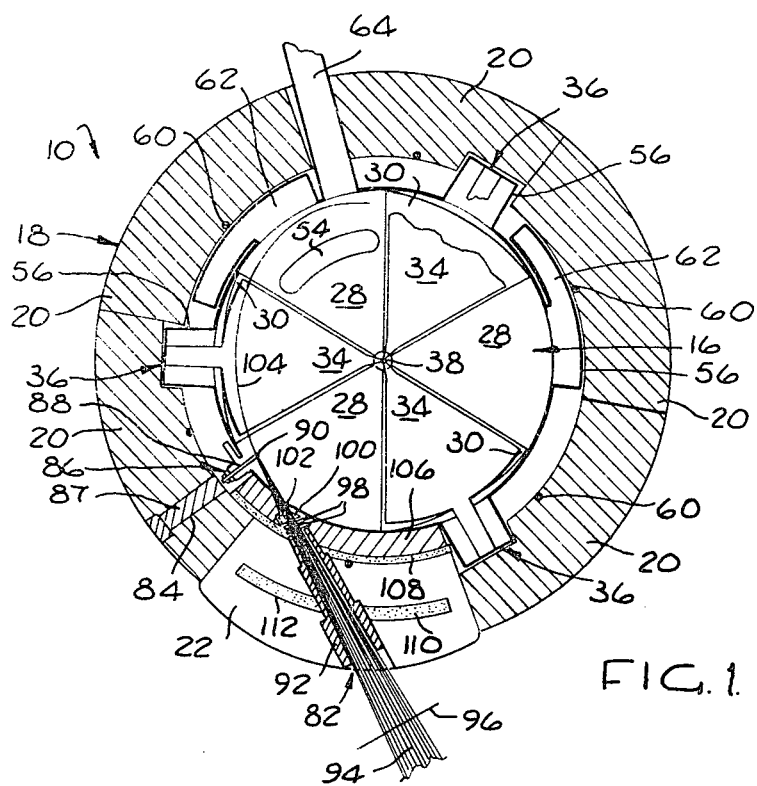
FIG. 1 shows a fragmentary, diagrammatic, sectional elevation through the plane of the accelerator zone of one embodiment of an isochronous cylotron in accordance with this invention.
Figure 2:
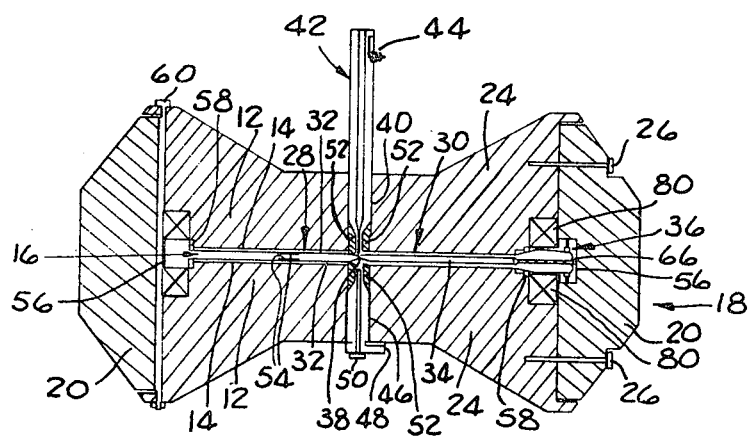
FIG. 2 shows a fragmentary, diagrammatic, sectional elevation through a plane normal to the plane of the accelerator zone, of the cyclotron of FIG. 1.

With reference to FIGS. 1 to 3 of the drawings, reference numeral 10 refers generally to an isochronous cyclotron for use in neutron therapy, and comprising a pair of opposed, spaced pole shoes 12 having their adjacent inner surfaces 14 defining an accelerator zone 16, and a magnet yoke 18 shaped to substantially enclose the accelerator zone 16 and constitute a neutron attenuation shield for neutrons produced in the cyclotron 10.

The magnet yoke 18 is constituted by a plurality of magnet yoke sections 20 and a magnet yoke section 22, which are mounted on the pole shoes 12 and pole shoe sections 24 by means of spaced bolts 26. The magnet yoke sections 20 and 22 are of generally truncated sector configuration, and are separate from each other to facilitate handling of the sections and assembly of the cyclotron 10, and to facilitate removal of individual magnet yoke sections for replacement or to provide access to the interior of the cyclotron 10.

The cyclotron has an isochronous magnetic field with three symmetrically arranged radial hills 28, and three symmetrically arranged radial valleys 30 defined by the adjacent inner surfaces 14 of the pole shoes 12.

The radial hills 28 are constituted by radial hill shims 32 fixed to the adjacent inner surfaces 14 of the pole shoes 12.

The cyclotron 10 has three hollow accelerating dee electrodes 34 positioned in each valley 30, with each dee electrode 34 having a radio-frequency resonator 36 operatively associated therewith.

The cyclotron 10 has a narrow accelerator zone 16, and the compactness of the cyclotron 10 is increased by positioning of the dee electrodes 34 in the valleys 30.

The dee electrodes 34 are to be operated in phase with each other, and are connected together at 38 at the centre of the accelerator zone 16.

The cyclotron 10 has a transmission bore 40 extending along the polar axis of one of the pole shoes 12, with the transmission bore having a co-axial radio-frequency transmission line 42 located in the transmission bore 40 and connected to the dee electrodes 34 at the common connection point 38.

Connection of the dee electrodes to the transmission line 42 at the centre assists in axially stabilising the dee electrodes 34 to combat frequency variations under pulsed dee voltages during use.

The radio-frequency transmission line 42 has an inductive coupling means 44 for coupling the transmission line 42 to a radio-frequency power source in the form of a radio-frequency oscillator or power amplifier (not shown).

The cyclotron 10 further has means for providing charged particles for acceleration within the accelerator zone, in the form of a loading passage 46 extending along the polar axis of the opposed pole shoe 12 to that having the transmission bore 40.

The loading passage 46 has a vacuum lock 48 of conventional type, and an ion source positioning member 50 is used to provide a suitable ion source in the accelerator zone 16.

The cyclotron 10 includes central magnetic steel inserts 52 to give the correct magnetic field distribution in the central region of the accelerator zone 16.

The cyclotron 10 has flat coils 54 mounted on the radial hill shims 32 to improve the isochronisation of the magnetic field and/or to reduce unwanted harmonic components in the magnetic field during use.

The cyclotron 10 further has a vacuum chamber enclosing the accelerator zone 16, the dee electrodes 34 and the radio-frequency resonators 36.

The vacuum chamber is defined by the adjacent inner surfaces 14 of the pole shoes 12, and by an annular generally channel-shaped vacuum member 56 surrounding the accelerator zone and having its free edges 58 sealingly secured to the opposed pole shoes 12.

In assembly of the cyclotron 10, the pole shoes 12 and vacuum member 56 with the dee electrodes 34 and the radio-frequency resonators 36 may be assembled as a unit.

The vacuum member 56 may itself constitute a precision spacer for the pole shoes 12, or additional precision spacers of non-magnetic material either connected to or separate from the vacuum member 56 may be used.

The pole shoes 12 may be secured together by means of circumferentially spaced tension bolts 60.

To ensure correct alignment of the pole shoes 12, accurately positioned complementary bore and spigot formations may be provided in the pole shoes 12.

The adjacent inner surfaces 14 of the pole shoes 12 which define the accelerator zone 16 and are exposed to the dee electrodes 34, are coated with thin, water-cooled copper plates.

The cyclotron 10 has internal vacuum pump means in the form of cryogenic pumps or a combination of titanium sublimation and ion pumps (not shown) provided in the spaces 62 to maintain a high vacuum in the accelerator zone 16 during use.

The cyclotron 10 further has a radial vacuum conduit 64 extending radially through the magnet yoke 18 for connection to an external vacuum pumping system.

Pressure measuring devices may further be associated with the radial vacuum conduit 64.

As can be seen in particular in FIG. 3 of the drawings, the dee electrodes 34 have their stem portions 66 mounted on the vacuum member 56 to provide a sufficiently rigid location of the dee electrodes 34 to provide mechanical stability for the dees especially when using pulsed dee voltages.

Each radio-frequency resonator 36 extends radially, and comprises a pair of flat, narrow inner conductor plates 68 mounted on opposed sides of the stem portion 66, and two flat, wider outer conductor plates 70 on opposed sides of the stem portion 66 and laterally spaced from the inner conductor plates 68.

Each outer conductor plate 70 has a flexible hinge 72, and has its outer extremity connected to its inner conductor plate 68 by means of a flexible short-circuit plate 74.

Each radio-frequency resonator 36 further includes a pair of opposed adjustment members 76 which extend from the outer conductor plates 70, sealingly through the walls defining the vacuum member 56, to allow for adjustment of the distance between each pair of plates 68 and 70 in order to change the characteristic impedence of the radio-frequency resonator 36, and therefore its resonating frequency.

The short-circuit plates 74 are cooled by cooling pipes 78.

with the particular construction of the radio-frequency resonators 36, energy dissipation during use will tend to be reduced. Applicant believes that under continuous operation the maximum radio-frequency energy dissipation of the whole system in the cyclotron 10, can be less than about 60 kW for a 30 kV peak voltage on the dee electrodes 34 for a cyclotron accelerating deuterons to 40 MeV.

The cyclotron 10 further includes an electromagnetic coil system comprising two annular coils 80 which surround the pole shoes 12.

The cyclotron 10 further has a neutron beam outlet 82 provided in the magnet yoke section 22 for emission of a neutron beam produced in the cyclotron 10.

The cyclotron 10 further has an internal target zone for a target device, with the target zone including a target admission zone 84 to provide access to the target zone.

The cyclotron 10 has a removable target devide 86 positioned in the target zone.

The target device 86 has a stem 88 with a beryllium target 90 provided thereon.

The target admission zone 84 has a shielding plug 87 removabley located therein.

The shielding plug 87 is of a suitable neutron shielding material, and the target admission zone 84 and the plug 87 are complementarily stepped to combat emission of stray neutrons produced within the cyclotron, out of the targate admission zone 84.

The target device 86 has conventional liquid cooling tubes (not shown) leading through the stem 88 to the target 90.

The target device 86 is adjustable to permit adjustment of the circumferential position of the target 90 and of the extent to which the target 90 projects into the accelerator zone 16. Thus by appropriate adjustment, the peak of a neutron flux beam produced on the target 90, can be made to coincide with the axis of the neutron beam outlet 82.

The neutron beam outlet 82 is shaped to removably receive suitable collimators of different sizes, to vary the radiation field size of a neutron beam emitted from the neutron beam outlet.

In FIG. 1 of the drawings, a suitable collimator 92 is shown in position in the nuetron beam outlet, and a neutron beam 94 is shown diagrammatically being emitted through the collimator 92 out of the cyclotron 10.

The line 96 extending across the neutron beam 94 in FIG. 1 of the drawings, indicates where the centre of an affected area of a patient to be treated with the neutron beam 94, would be placed during treatment at the core of the neutron beam 94.

The neutron dose rate and integrated neutron dose can be measured by placing one or more monitors 98 within the magnet yoke 18 in the path of the neutron beam 94.

This zone can also be used for a mirror and light system of conventional type, to aid setting up of a patient for treatment.

The cyclotron 10 may further include an absorber for gamma rays positioned at position 100 to shield a patient and therapy staff against gamma rays from the decay of radio-active isotopes produced in the target 90 or in the vicinity of the target 90.

The cyclotron 10 further includes a thin metal window 102 in the vacuum member 56, through which the neutron beam 94 emerges.

With the particular cyclotron 10 illustrated in FIGS. 1 to 3, it is believed that a cyclotron accelerating deuterons to an energy of about 40 MeV can be realised. Thus an approximately 20μA deuteron beam 104 impinging on the target 90, can be expected to produce a fast neutron beam 94 with a dose rate of about 100 rad/min at a distance of about 1.6 m from the target 90 on the line 96.

The cyclotron 10 is expected to have a diameter of about 3 m, and the magnet yoke sections 20 would be expected to have a wall thickness of about 35 to 45 cm to provide the magnetic flux requirements of the cyclotron 10.

With this arrangement, applicant believes that the wall thickness of the magnet yoke sections 20 together with the thickness of the pole shoe sections 24, will be sufficient to attenuate neutron fluxes of low intensity coming off at wide angles to the forward neutron peak zone of the neutron beam 94, as well as stray neutrons arising in the cyclotron, to a patient tolerable level in a neutron therapy installation incorporating the cyclotron 10. In this connection it should further be noted that the radial vacuum conduit 64 is on the opposed side of the neutron beam outlet 82, so that the cyclotron 10 will again assist in shielding a patient to be treated, from the stray neutrons which may escape from the radial vacuum conduit 64.

While it is believed that the neutron attenuation will be sufficient to provide a radiation background in a therapy room which is patient tolerable, it is believed that the radiation background will always exceed the tolerance dose for therapy staff during the treatment of a patient. Thus the cyclotron 10 will, for use in neutron therapy, be provided in a neutron therapy installation having biological shielding of conventional type.

However, auxiliary neutron shield means will be required in the forward peak zone of the neutron beam 94, to shield the body of a patient being treated, against the intense flux of high energy neutrons in the forward peak zone of the neutron beam.

The cyclotron 10 therefore includes auxiliary neutron shield means.

The auxiliary neutron shield means comprises an internal neutron attenuation shield 106 which is mounted within the inner periphery of the magnet yoke 18 in the forward peak zone of the neutron beam 94.

The internal neutron attenuation shield 106 is of any conventional non-magnetic material, such as copper.

The auxiliary neutron shield means further comprises inner and outer neutron moderating shields 108 and 110. The neutron moderating shields 108 and 110 may be of any conventional type. Thus, for example, they may comprise any suitable hydrogen containing moderating material, containing suitable known elements such as boron or cadmium for the capture of thermal neutrons.

The inner neutron moderating shield 108 is provided along the inner periphery of the magnet yoke section 22 between the magnet yoke section 22 and the internal neutron attenuation shield 106.

The outer neutron moderating shield 110 is provided in a cavity 112 in the magnet yoke section 22.

The magnet yoke section 22 comprises two separate parts which are fitted together along the plane of the accelerator zone 16, thereby allowing the cavities 112 to be formed, and to filled with the neutron moderating material.

The auxiliary neutron shield means is further provided by the magnet yoke section 22 having a greater wall thickness than the magnet yoke sections 20.

The inner and outer neutron moderating shields 108 and 110 serve to moderate neutrons with energies up to a few MeV emerging from the internal neutron attenuation shield 106 and from the inner peripheral portion of the magnet yoke section 22.

The auxiliary neutron shield means is such that it is sufficient to attenuate neutron and gamma radiation in the forward peak zone to provide a combined neutron and gamma radiation dose rate of less than about 1% of that in the neutron beam 94 emitted from the neutron beam outlet 82 during use.

Since the auxiliary shield means comprises part of the cyclotron 10, shorter distances can be employed between the target 90 and the positioning of an affected area of a patient to be treated, thereby allowing for lower neutron production rates by the cyclotron 10. In addition, by having the auxiliary neutron shield means in close proximity to the target 90, the mass of shielding required can be reduced thereby allowing for a reduction in the mass of the cyclotron.

The maximum deuteron beam current which could be accelerated with a dee voltage of 30 kV amounts to about 100 $\mu$A, while a beam current of only about 20 $\mu$A should be required to deliver a neutron dose rate of about 100 rad per minute with the cyclotron 10.

Applicant believes therefore that it should be possible to pulse the dee voltage with a 20% duty cycle, using, for example, two millisecond pulses every 10 milliseconds, thereby reducing the time average of the power delivered by the radio-frequency power supply from a maximum value of 60 kW to 12kW.

This provides the advantage that smaller and more economical radio-frequency power supplies with the capability of handling the peak power in the pulses, could be used.

A further advantage is that, because the power consumption of the radio-frequency system rises with the square of the dee voltage and the beam current accelerated from the ion source also depends roughly on the square of the dee voltage, higher dee voltages can therefore be used in combination with shorter pulses while constant average beam current and radio-frequency power consumption is maintained.

Higher dee voltages lead to a reduction of the number of turns through which the particles are accelerated in the cyclotron, thereby relaxing the requirements on the isochronisation of the magnetic field.

Pulsing of the radio-frequency system also makes it possible to use short pulses at very low repetition rates to check the properties of the neutron beam after the patient is set up for treatment and just before treatment commences.

If a relatively high frequency (about 35 MHz) of accelerating voltage is applied to the dee electrodes 34, and a high dee to ground capacity is provided by the dee to ground spacings being between about 15 and 25 mm, the relatively short quarter wave transmission lines with inner and outer conductor plates 68 and 70 should provide suitable radio-frequency resonators 36.

With particular reference to FIGS. 4 and 5 of the drawings, reference numeral 10.1 refers generally to a cyclotron in accordance with this invention, having an alternative construction to the cyclotron 10 of FIGS. 1 to 3 of the drawings.

The essential features of the cyclotron 10.1 do however correspond with the essential features of the cyclotron 10. Corresponding features of the cyclotron 10.1 which correspond with those of the cyclotron 10, are therefore indicated by corresponding reference numerals having the suffix "0.1".

The cyclotron 10.1 has its pole shoe sections 24.1 of hexagonal configuration, instead of the circular configuration of the pole shoe sections 24 of the cyclotron 10.

Thus spaces 114 are left between the circular pole shoes 12.1 and the pole shoe sections 24.1.

Within the spaces 114, steel pillars 116 are provided which constitute precision spacers and support the pole shoes 12.1 and pole shoe sections 24.1 relatively to each other.

The steel pillars 116 can be welded to one of the pole shoe sections 24.1 and have their free end surfaces precision machined for accurate spacing of the accelerator zone 16.1.

The pole shoes 12.1 can be secured together by means of tension bolts 60.1 passing through one of the pole shoe sections 24.1 and into the steel pillars 116.

The magnet yoke sections 20.2 and 22.1 can be made out of flat plates of magnetic steel, and can be secured to the pole shoe sections 24.1 by means of bolts 26.1.

Openings 118 may be provided in the magnet yoke section 20.1 for the radio-frequency resonators.

With reference to FIG. 6 of the drawings, reference numeral 10.2 refers generally to a cyclotron having yet a further alternative form of construction to the cyclotrons 10 and 10.1.

In FIG. 6 of the drawings, corresponding parts to those of the cyclotrons 10 and 10.1, are again indicated by corresponding reference numerals, having the suffix "0.2".

Experiments have shown that it should be possible to use protons of 35 MeV and higher energies to produce suitable neutron beams on beryllium targets for neutron therapy. However at 35 MeV, approximately six times higher proton beam intensities, compared to deuteron beam intensities of the same nergy, will be required.

However, when using protons, the pole shoe diameters would be reduced by about 40%, leading a decrease of the mass of the cyclotron from about 60 tonnes (the estimated mass of the cyclotron of FIGS. 1 to 3) to about 30 tonnes.

For such pole shoes 12.2 of reduced size, the cyclotron construction illustrated in FIG. 6 of the drawings, would be appropriate. The cyclotron 10.2 has its magnet yoke 18.2 in the form of an annular ring comprising a plurality of ring segments 20.2.

In this embodiment, the ring segments 20.2 constitute precision spacers for the pole shoes 12.2.

In this embodiment, the pole shoe sections 24.2 and the magnet yoke sections 20.2 having complementary spigot formations 120 and socket formations 122 for correct alignment of the pole shoe sections 24.2.

The pole shoe sections 24.2 are secured to the magnet yoke sections 20.2 by means of tension bolts 60.2.

With reference to FIG. 7 of the drawings, reference numeral 124 refers generally to a neutron therapy installation having a cyclotron 10.3 in accordance with this invention, operatively mounted therein.

The cyclotron 10.3 corresponds in all respects with the cyclotron 10 of FIGS. 1 to 3 of the drawings, but has pivot means for pivotally supporting it in position in the neutron therapy installation 124.

The cyclotron 10.3 thus has pivot bores 126 in the opposed pole shoe sections 24.3 to allow pivotal displacement of the cyclotron 10.3 about its polar axis extending normally to the plane of the accelerator zone.

The neutron therapy installation includes opposed pivot shafts 128 having their free ends extending into the pivot bores 126, and connected within the pivot bores 126 via suitable bearings 130.

The therapy installation 124 includes suitable driving means (not shown) for pivotally displacing the cyclotron 10.3 about the pivot shafts 128 during use. The driving means may, for example, comprise any suitable low speed, high torque driving means such as a hydraulic driving system.

The neutron therapy installation 124 is constructed out of conventional biological shielding means such as concrete walls 132 and a shielding ceiling slab (not shown).

The installation 124 has a therapy zone 134 and an inlet maze 136.

The therapy zone 134 includes one or more movable plinths 138 for supporting patients 140 to be treated.

The plinths 138 are vertically and laterally adjustable.

The therapy zone 134 further includes an elevated platform 140 on which one of the plinths 138 may be mounted.

The therapy zone 134 further has a neutron moderating pit provided in its floor, for moderating stray neutrons which arise during use.

The therapy zone can also act as an assembly and servicing zone for the cyclotron.

By appropriate pivotal displacement of the cyclotron 10.3, the direction of the neutron beam can be altered along a vertical plane in the plane of the accelerator zone, to provide for effective treatment of patients.

The therapy installation 124 includes an elevated service zone (not shown) which is spaced above the therapy zone 134.

The service zone may conveniently include a rotatably mounted collimator holder to hold a plurality of collimators at circumferentially spaced intervals, and automatic transfer means for transferring collimators between the collimator holder and the neutron beam outlet of the cyclotron 10.3, when the cyclotron 10.3 has been pivotally displaced so that the neutron beam outlet is directed vertically upwardly.

Thus collimators can be replaced to provide different radiation field sizes, or when a particular collimator has become too radio-active.

The therapy installation may further include crane means for use in handling components of the cyclotron 10.3 during maintenance or servicing.

With reference to FIG. 8 of the drawings, reference numeral 10.4 refers generally to a cyclotron corresponding with the cyclotron 10 of FIGS. 1 to 3, except that it is pivotally supported for pivotal displacement during use.

The cyclotron 10.4 has pivot shafts 144 extending outwardly from its opposed pole shoe pieces, with each pivot shaft having a gear wheel 146 mounted thereon.

The gear wheels 146 pivotally support the cyclotron 10.4 on suitable support rails 148 in the form of linear gear rails having teeth to mesh with the gear wheel teeth.

Thus by displacing the gear wheels 146 along the support rails 148 the direction of the neutron beam emitted by the cyclotron 10.4 can again be varied in a vertical plane to provide effective treatment of patients.

It will be appreciated that with a suitable choice of radii of the gear wheels 146 with respect to the orbit radius of the deuteron beam on the target, a system where the patient will have to be moved mainly in a vertical direction when using neutron beams in different directions, can be provided.

The support rails 148 may, if desired, be inclined to the horizontal. In this embodiment by choice of an appropriate inclination, horizontal and vertical neutron beam directions may be made to coincide, while a patient would have to be displaced slightly for other beam directions.

Figure 9:
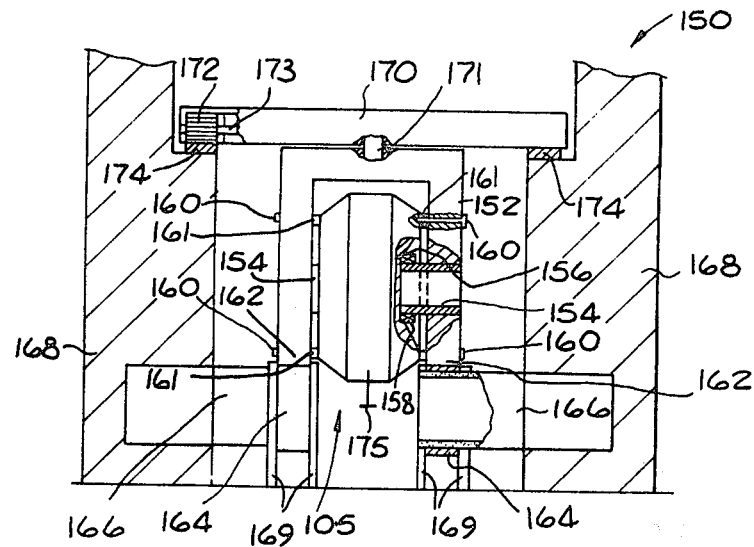
FIG. 9 shows a fragmentary, diagrammatic, partly sectional, end elevation of a neutron therapy installation having a cyclotron in accordance with this invention, pivotally mounted therein to provide to an isocentric therapy system.
Figure 10:
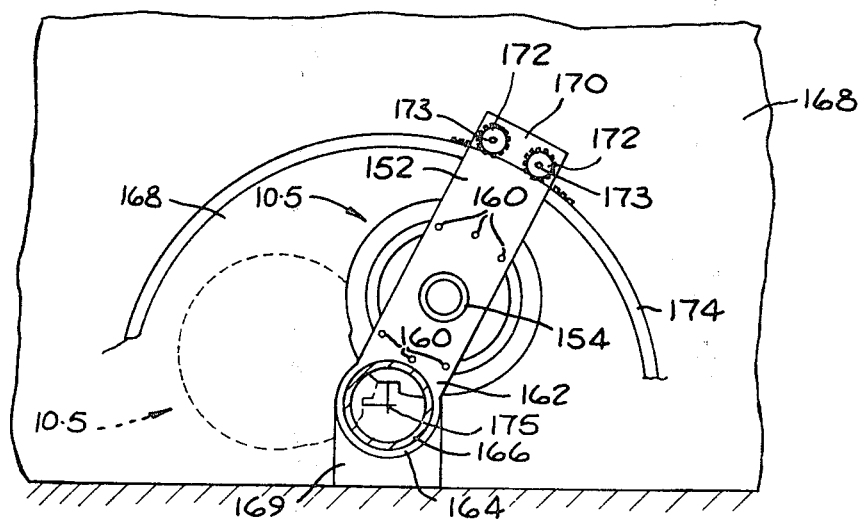
FIG. 10 shows a diagrammatic, fragmentary, side elevation of the installation of FIG. 9.

With reference to FIGS. 9 and 10 of the drawings, reference numeral 150 refers generally to a neutron therapy installation having a cyclotron 10.5 pivotally mounted therein to provide a fully isocentric therapy facility.

The cyclotron 10.5 corresponds with the cyclotron 10 of FIGS. 1 to 3 of the drawings, but is pivotally mounted in a U-shaped pivot frame 152.

The pivot frame 152 has two opposed hollow shafts 154 which extend inwardly into sockets 156 provided in the pole shoe pieces of the cyclotron 10.5, and are engaged in the sockets 156 via bearings 158.

The pivot frame 152 has bolts 160 extending therethrough and engaging with the cyclotron via spacers 161, to fix the cyclotron to the frame 152.

By removing the bolts 160, the cyclotron 10.5 can be pivotally displaced about the hollow shafts 154 for servicing or maintenance.

The hollow shafts 154 provide access to the central regions of the cyclotron 10.5.

The pivot frame 152 has a pair of opposed legs 162, with each leg 162 having a pivot bore 164 pivotally mounted on a hollow support axle 166.

The hollow support axles 166 are mounted in opposed walls 168 of the installation 150, and are mounted on support members 169 on opposed sides of the pivot bores 164.

The pivot frame 152 has a pivot beam 170 pivotally mounted thereon via a pivot shaft 171.

The pivot beam 170 has a pair of guide gear wheels 172 pivotally mounted at each end thereof on a pair of axles 173.

The guide gear wheels 172 co-operate with curved, complementarily toothed guide rails 174 which are concentric with the support axles 166 and are provided in the opposed walls 168.

The pivot bores 164 are positioned so that their polar axes will intersect the core of a neutron beam emitted from the neutron beam outlet during use as indicated by reference numeral 175, in the treatment zone of such a beam where the center of an affected area of a patient to be treated, would be positioned during treatment. Thus a fully isocentric treatment facility is provided.

The support axles 166 are hollow to increase the space available for positioning of a patient for treatment, and can accommodate body portions of a patient during treatment.

By mounting the pivot beam 170 on the pivot frame 152 via the pivot shaft 171, inaccurate alignment of the guide rails 174 can be accommodated.

The cyclotron 10.5 can conveniently be displaced by suitable driving means (not shown) driving the gear wheels 172.

Figure 11:
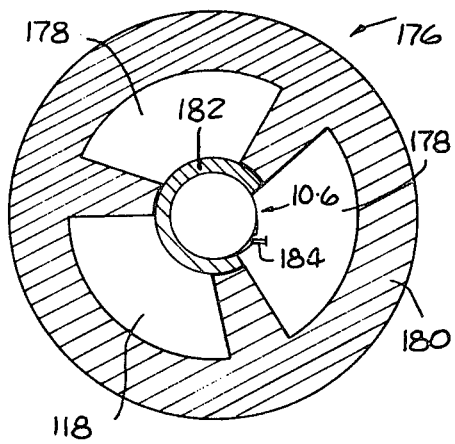
FIG. 11 shows a fragmentary, diagrammatic, sectional plan view of an alternative embodiment of a neutron therapy installation in accordance with this invention, having a cyclotron in accordance with this invention pivotally supported therein for pivotal displacement about a vertical axis.

With reference to FIG. 11 of the drawings, reference numeral 176 refers to yet a further embodiment of a neutron therapy installation in accordance with this invention.

The therapy installation 176 has a cyclotron 10.6 operatively mounted therein.

The cyclotron 10.6 corresponds with the cyclotron 10 of FIGS. 1 to 3 of the drawings, except that it is pivotally supported on the floor of the installation 176, on a turntable support, for pivotal displacement about a vertical axis extending normally to the plane of the accelerator zone.

The installation 176 has three therapy zones 178 with appropriate biological shielding 180 of conventional type, circumferentially spaced about the cyclotron 10.6.

The cyclotron 10.6 has a semi-annular biological shield 182 mounted on its periphery, to rotate with the cyclotron 10.6.

The shield 182 provides biological shielding against stray neutrons in two of the therapy zones 178 while a patient is being treated in the therapy zone 178 having the neutron beam 184 directed into it.

Thus while a patient is being treated in one of the therapy zones 178, patients can be set up for treatment in the remaining therapy zones thereby improving the rate at which patients can be treated.

Figure 12:
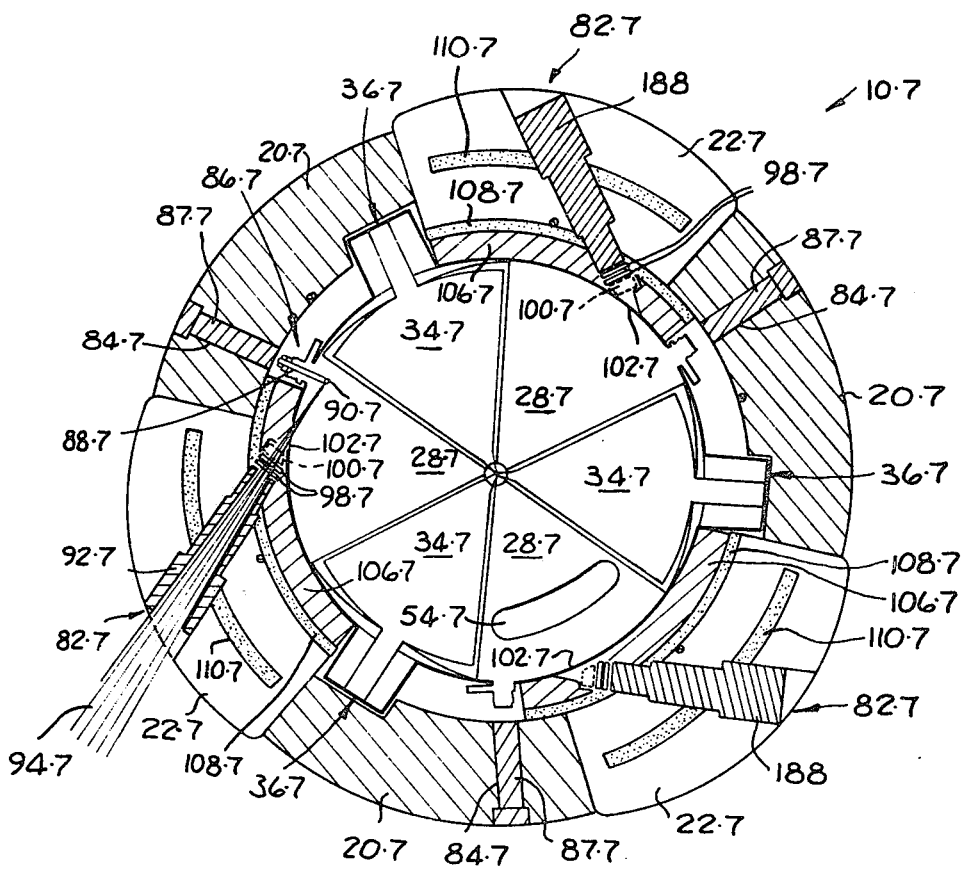
FIG. 12 shows a fragmentary, diagrammatic, sectional elevation through the plane of the pole gap of yet a further alternative embodiment of an isochronous cyclotron in accordance with this invention.

With reference to FIG. 12 of the drawings, reference numeral 10.7 refers generally to yet a further embodiment of an isochronous cyclotron in accordance with this invention. The cylotron 10.7 corresponds with the cyclotron 10 of FIGS. 1 to 3 of the drawings, and corresponding parts to those of the cyclotron 10, are indicated by corresponding reference numerals except that the suffix "0.7" has been added.

The cyclotron 10.7 has three neutron beam outlets 82.7 with three appropriately positioned target admission zones 84.7 provided in the three magnet yoke sections 20.7, and the neutron beam outlets 82.7 are provided in three magnet yoke sections 22.7 which correspond with the magnet yoke section 22 of FIG. 1.

One of the target admission zones 84.7 is shown having a target device 86.7 located in its associated target zone, and the corresponding neutron beam outlet 82.7 is shown having a collimator 92.7 located therein.

The remaining two target admission zones 84.7 do not have target devices located in their associated target zones, and their associated neutron beam outlets 82.7 have closed shielding members 188 located therein.

All the target admission zones 84.7 are shown having shielding plugs 87.7 located therein.

Thus the two target admission zones 84.7 and the two neutron beam outlets 82.7 which are not in use, are effectively shielded, while the one neutron beam outlet 82.7 is in use.

It will be noted that the dee electrodes 34.7 and their radio-frequency resonators 36.7 are positioned so that they are not in the neutron peak zones of any of the neutron beams produced in the cyclotron 10.7.

If desired, target devices 86.7 may be provided in all three target zones and, when not in use, they may be adjusted via the target admission zones 84.7 to retract their targets 90.7 out of the path of the accelerated beam in the accelerator zone of the cyclotron 10.7.

The cyclotron 10.7 can conveniently be used for neutron therapy in a neutron therapy installation corresponding generally to the installation 176 illustrated in FIG. 11 of the drawings.

Since the cyclotron 10.7 will be stationary, having its neutron beam outlets 82.7 directed into the separate therapy zones 178, additional biological shielding can be provided on the cyclotron 10.7 or the wall thicknesses of the magnet yoke sections 20.7 and 22.7 can be increased to provide improved shielding.

The embodiments of the cyclotron as illustrated in the drawings, and the embodiments of a neutron therapy installation including a cyclotron as illustrated in the drawings, can provide various advantages. Thus, one or more embodiments of the invention as illustrated in the drawings, can provide one or more of the following advantages:

1. The specific design of the complete magnetic circuit, including the pole pieces and the magnet yoke, provides the advantage that the magnet steel is used efficiently and the length of the magnetic circuit is minimised, thereby allowing for a substantial reduction in the mass of the magnet steel in comparison with typical cyclotrons of conventional construction. Thus applicant believes that in comparison with typical cyclotrons of conventional construction, the cyclotron in accordance with this invention as illustrated in the drawings, can have the mass of the magnet steel reduced from about 55 metric tonnes to about or less than about 30 metric tonnes for the acceleration of protons to 35 MeV, and from about 150 metric tonnes to about 60 metric tonnes for the acceleration of deuterons to 40 MeV;

2. The particular construction as illustrated in the drawings, can also lead to compact electro-magnetic coils with a power consumption of less than about 30 kW;

3. The particular arrangement of the magnetic steel in the cyclotron as illustrated in the drawings, also serves to attenuate neutrons produced in the cyclotron and, together with the auxiliary neutron shielding provided in the forward peak zone of the neutron beam in close proximity to the internal neutron producing target, provides effective overall neutron attenuation to safeguard a patient being treated. Additionally, by merely attenuating unwanted neutrons to patient tolerable levels in a therapy zone, compactness of the cyclotron is maintained;

4. Construction of the cyclotron and its associated power supplies is simplified by the fact that only one type of charged particle is accelerated to a fixed energy, and that an internal cyclotron target is used. Thus the need for a conventional type of beam deflecting system, a beam transporting system and separate shielding as would be required for an external neutron producing target for neutron therapy, are eliminated;

5. Neutron therapy is appreciably facilitated if neutron beams of differing directions are available for use. An isocentric therapy system will be even more advantageous. Conventional cyclotrons for neutron therapy often only have neutron beams of fixed direction. Alternatively, they employ either a system of stationary electro-magnets and shields to provide charged particle beams of differing directions in order to produce neutron beams of differing directions, or employ a movable system of electro-magnets and shielding to provide a neutron beam facility approaching isocentricity. The compact construction and reduced mass of the cyclotron in accordance with this invention as illustrated in the drawings, makes it possible to mount the cyclotron for pivotal displacement by relatively simple means in order to provide neutron beams of differing directions. In this regard the embodiment as illustrated in FIGS. 9 and 10 of the drawings, is particularly advantageous since it provides a fully isocentric therapy system;

6. Because the magnet steel and auxiliary neutron shielding in the forward peak zone reduce unwanted neutron and gamma radiation to patient compatible levels, the cyclotron of this invention can be installed in a neutron therapy zone itself. Thus the biological shielding of the therapy zone also acts as biological shielding for the cyclotron. Thus the need for an independent cyclotron vault of large area and its associated biological shielding can be eliminated;

7. The modular constructions, as illustrated in the drawings, can facilitate servicing and maintenance. In addition, those parts of the cylotron which have become activated by the neutron beam during use, can be temporarily removed during servicing, or can be replaced if they become too radio-active;

8. As illustrated in FIGS. 1 to 3 of the drawings, the particular radio-frequency resonator can be completely enclosed within the vacuum member and within the magnet yoke, so that the need for additional shielding about the radio-frequency resonators is reduced or totally eliminated.

In view of the above, a cyclotron in accordance with this invention embodying the above advantages, should be able to be provided more cheaply for neutron therapy than typical cyclotrons of conventional construction. Thus such a cyclotron should find application as a single purpose cyclotron for neutron therapy in a hospital complex.

Applicant further believes that the cyclotron as illustrated in the drawings, could be used for in vivo, in vitro, whole body and conventional neutron activation analysis with both slow and fast neutrons by either using the neutron beam as employed for neutron therapy or by suitable pulsing thereof by pulsing the ion source and/or the dee voltage.

It will be appreciated that when the cyclotron is mounted in a radio-therapy installation with sufficient biological shielding, the internal cyclotron beam could conveniently also be used for isotope production on internal targets.

I claim:

1. A light, compact cyclotron suitable for use in neutron therapy, and capable of being moved to change the direction of an exiting neutron beam comprising:
   (a) a pair of opposed, spaced pole shoes having their adjacent inner surfaces defining an accelerator zone, the surfaces being adapted to constitute magnetic equipotential surfaces which establish a magnetic field configuration for the cyclotron during use,
   (b) an electromagnetic coil system around the pole shoes and adapted for connection to an electrical power source for generating the cyclotron magnetic field between the pole shoe surfaces,
   (c) a magnet yoke to provide a magnetic flux return path for the pole shoes, the magnet yoke together with the pole shoes providing a low magnetic resistance relatively to that of the accelerator zone, and the magnet yoke being shaped to substantially enclose the accelerator zone to constitute, together with the pole shoes, a neutron attenuation shield for neutrons produced in the cyclotron,
   (d) at least one hollow accelerating dee electrode positioned in the accelerator zone, and having a radio frequency resonator associated therewith,
   (e) a vacuum chamber enclosing the acclerator zone and each dee electrode,
   (f) means for providing charged particles for acceleration within the accelerator zone,
   (g) a target zone for a target device, and
   (h) a neutron beam outlet in the magnet yoke for emission of a neutron beam produced in the cyclotron.

2. A cyclotron according to claim 1, in which the adjacent inner surfaces of the pole shoes are shaped to define at least three hills and valleys to establish an isochronous magnetic field configuration during use.

3. A cyclotron according to claim 2, in which the hills and valleys are radial.

4. A cyclotron according to claim 2, having a dee electrode positioned in each valley, with each dee electrode having a radio frequency resonator associated therewith.

5. A cyclotron according to claim 4, in which the dee electrodes are connected to each other at the centre of the accelerator zone.

6. A cyclotron according to claim 5, having a transmission bore extending along the polar axis of one of the pole shoes, having a radio-frequency transmission line located in the transmission bore and connected to the dee electrodes at the centre of the accelerator zone, and having coupling means for coupling the transmission line to a radio-frequency power source.

7. A cyclotron according to claim 1, having auxiliary neutron shield means in the forward neutron peak zone of a neutron beam produced in the cyclotron to attenuate neutron and gamma radiation in the forward peak zone to provide a combined neutron and gamma radiation dose rate of less than about 3% of that in a neutron beam emitted from the neutron beam outlet during use.

8. A cyclotron according to claim 7, in which the auxiliary neutron shield means comprises a neutron attenuation shield and a neutron moderating shield.

9. A cyclotron according to claim 8, in which the neutron attenuation shield is provided within the magnet yoke and the neutron moderating shield is provided in the magnet yoke.

10. A cyclotron according to claim 2, in which the neutron beam outlet is shaped to removably receive a collimator to control the radiation field size of a neutron beam emitted from the neutron beam outlet.

11. A cyclotron according to claim 2, in which the vacuum chamber is defined by the adjacent inner surfaces of the pole shoes and by an annular channel member surrounding the accelerator zone and having its free edges sealingly secured to the opposed pole shoes.

12. A cyclotron according to claim 2, in which the magnet yoke comprises a plurality of separate yoke sections which together constitute the magnet yoke.

13. A cyclotron according to claim 1, in which each radio-frequency resonator extends radially and is enclosed within the magnet yoke.

14. A cyclotron according to claim 13, in which each radio-frequency resonator comprises a flat, narrow inner conductor plate mounted on the dee, and two flat, wider outer conductor plates on opposed sides of and laterally spaced from the inner conductor plate, with the outer conductor plates connected to the inner conductor plate by means of short circuit plates.

15. A cyclotron according to claim 14, in which each outer conductor plate includes a flexible hinge, in which each short circuit plate is flexible, and in which frequency adjustment means extends from each outer conductor plate to allow for adjustment of the characteristic impedance of each radio frequency resonator.

16. A cyclotron according to claim 1, having pivot means for pivotally mounting the cyclotron to allow variation of the direction of a neutron beam emitted from the neutron beam outlet during use.

17. A cyclotron according to claim 16, in which the pivot means comprises pivot bores in opposed sides of the cyclotron, for receiving pivot shafts to pivotally support the cyclotron.

18. A cyclotron according to claim 16, in which the pivot means comprises two pivot shafts extending outwardly from opposed sides of the cyclotron, each pivot shaft having a support gear wheel mounted thereon for pivotally supporting the cyclotron on suitable support rails in the form of linear gear rails having teeth to mesh with the gear wheel teeth.

19. A cyclotron according to claim 16, in which the polar axis of the pivot means extends normally to the plane of the accelerator zone along the polar axis of the cyclotron.

20. A cyclotron according to claim 16, in which the pivot means comprises a pivot frame in which the cyclotron is mounted, the pivot frame having a pair of opposed supporting legs, with each supporting leg having a pivot bore for pivotally mounting the frame on a pair of support axles, and the pivot frame having a pivot beam mounted thereon, with the pivot beam having guide gear wheels mounted at its opposed ends to co-operate with a pair of curved, complementarily toothed guide rails positioned concentrically with the pivot bores to guide pivotal displacement of the cyclotron about the pivot bores, the pivot bores being positioned so that their axes will intersect the core of a neutron beam emitted from the neutron beam outlet during use, in the treatment zone of such a beam where the centre of an affected area of a patient to be treated would be positioned during treatment, thereby providing an isocentric therapy system.

21. A cyclotron according to claim 20, in which the cyclotron is pivotally mounted in the pivot frame.

22. A cyclotron according to claim 16, in which the pivot means comprises a turntable to support the cyclotron on a surface for pivotal displacement about a vertical axis.

23. A neutron therapy installation comprising biological shielding means to define the installation, and having a light, compact cyclotron for use in neutron therapy, mounted therein, and capable of being moved to change the direction of an exiting neutron beam,. the cyclotron comprising:
  (a) a pair of opposed, spaced pole shoes having their adjacent inner surfaces defining an accelerator zone, the surfaces being adapted to constitute magnetic equipotential surfaces which establish a magnetic field configuration for the cyclotron during use,
  (b) an electromagnetic coil system around the pole shoes and adapted for connection to an electrical power source for generating the cyclotron magnetic field between the pole shoe surfaces,
  (c) a magnet yoke to provide a magnetic flux return path for the pole shoes, the magnet yoke together with the pole shoes providing a low magnetic resistance relatively to that of the accelerator zone, and the magnet yoke being shaped to substantially enclose the accelerator zone to constitute, together with the pole shoes, a neutron attentuation shield for neutrons produced in the cyclotron,
  (d) at least one hollow accelerating dee electrode positioned in the accelerator zone, and having a radio frequency resonator associated therewith,
  (e) a vacuum chamber enclosing the accelerator zone and each dee electrode,
  (f) means for providing charged particles for acceleration within the accelerator zone,
  (g) a target zone for a target device, and
  (h) a neutron beam outlet in the magnet yoke for emission of a neutron beam produced in the cyclotron.

24. A neutron therapy installation according to claim 23, in which the cyclotron has pivot means for pivotally mounting the cyclotron to allow variation of the direction of a neutron beam emitted from the neutron beam outlet during use, and in which the installation has pivot support means for engaging with the pivot means.

25. A neutron therapy installation according to claim 24, in which the cyclotron has pivot means in the form of pivot bores in opposed sides thereof, and the pivot support means comprises opposed pivot shafts which extend into the pivot bores and have bearings mounted thereon which engage with the pivot bores.

26. A neutron therapy installation according to claim 24, in which the cyclotron has pivot means in the form of two pivot shafts extending outwardly from opposed sides thereof, with each pivot shaft having a support gear wheel mounted thereon, and the installation includes two linear gear support rails having teeth to mesh with the teeth of the gear wheels.

27. A neutron therapy installation according to claim 24, in which the pivot means comprises a pivot frame in which the cyclotron is mounted, the pivot frame having a pair of opposed supporting legs, with each supporting leg having a pivot bore, and the pivot frame having a pivot beam mounted thereon, with the pivot beam having guide gear wheels mounted at its opposed ends, and in which the pivot support means comprises two opposed support axles on which the pivot bores are mounted, and two opposed curved, toothed guide rails which are concentric with the support axles to co-operate with the guide gear wheels of the pivot beam and guide pivotal displacement of the cyclotron about the pivot bores, the pivot bores being positioned so that their axes will intersect the core of a neutron beam emitted from the neutron beam outlet during use, in the treatment zone of such a beam where the centre of an affected area of a patient to be treated would be positioned during treatment, thereby providing an isocentric therapy system.

28. A neutron therapy installation according to claim 23, in which the cyclotron has pivot means in the form of a turntable to support the cyclotron on the floor of the installation for pivotal displacement about a vertical axis, and in which the installation has a plurality of separate treatment rooms circumferentially spaced about the cyclotron, with each room having an access opening to register with the neutron beam outlet of the cyclotron.

* * * * *